United States Patent [19]

Mitscher

[11] 4,215,062
[45] Jul. 29, 1980

[54] ANTHRACYCLINE SYNTHESIS

[75] Inventor: Lester A. Mitscher, Lawrence, Kans.

[73] Assignee: University of Kansas Endowment Association, Lawrence, Kans.

[21] Appl. No.: 908,256

[22] Filed: May 22, 1978

[51] Int. Cl.$^2$ .................. C07C 87/10; C07C 49/74
[52] U.S. Cl. .................. 260/365; 260/351; 260/364; 260/376; 260/369
[58] Field of Search ............ 260/351, 364, 365, 369, 260/376, 383, 522

[56] References Cited

U.S. PATENT DOCUMENTS

| | | | |
|---|---|---|---|
| 3,721,684 | 3/1973 | Meyers et al. | 260/365 |
| 4,070,382 | 1/1978 | Kende et al. | 260/365 |
| 4,132,721 | 1/1979 | Bernardi et al. | 260/365 |

OTHER PUBLICATIONS

*Journal of the American Chemical Society*, vol. 99, p. 5518, 1977, Kelly et al.
*Tetrahedon Letters* p. 2383, 1977, Raynolds et al.
*Journal of American Chemical Society* vol. 98, pp. 1967–1969, 1976, Kend et al.
*Canadian Journal of Chemistry*, vol. 51, p. 466; 1973, Wong et al.
*Journal of Medicinal Chemistry*, vol. 17, No. 6 p. 659, 1974 Acton et al.
*Journal of the American Chemical Society* vol. 97, No. 15, p. 4425, 1975 Kende et al.
*Chemical Abstracts*, vol. 43, #2985f, "Polycyclic aromatic amines", G. M. Badger 1948.
*Chemical Abstracts* vol. 73 #17076i, "Catalytic action of quinones in the oxidation of 4-methyl meso-benzanthrane to mesopenzanthrone-4-carboxylic acid", W. Bradley and Kitti Shah, 1959.

*Primary Examiner*—Winston A. Douglas
*Assistant Examiner*—Raymond K. Lovington
*Attorney, Agent, or Firm*—Finnegan, Henderson

[57] ABSTRACT

A process for synthesizing doxorubicin and related compounds from aloe-emodin is disclosed. Intermediates useful in the preparation of doxorubicin and related compounds are also disclosed.

30 Claims, No Drawings

ANTHRACYCLINE SYNTHESIS

FIELD OF THE INVENTION

The present invention pertains to a technique for synthesizing doxorubicin and related compounds such as daunomycin and carminomycin, and the aglycones thereof. The present invention also pertains to intermediates useful in the synthesis of doxorubicin and related compounds.

BACKGROUND OF THE INVENTION

Doxorubicin is a known anthracycline antibiotic described, e.g., in U.S. Pat. No. 3,590,028. Doxorubicin, and the closely related compound daunomycin, are antineoplastic agents of established clinical utility. Doxorubicin hydrochloride, available from Adria Laboratories, Inc. under the trade name Adriamycin ®, has been approved by the Food and Drug Administration for use in clinical research, and is one of the most powerful anticancer drugs available against numerous forms of cancer.

At present, doxorubicin is produced commercially from a soil fungus by a fermentation process. A suitable fermentation technique for preparing doxorubicin is described in U.S. Pat. No. 3,590,028. Such techniques are inherently expensive and limit the types of molecules that can be produced. Because of the inherent disadvantages of presently available commercial techniques for producing doxorubicin and related compounds, substantial effort has been devoted to developing processes for producing such compounds by chemical synthesis.

Techniques for the synthesis of anthracycline antibiotics such as doxorubicin are known. See, e.g., Wong et al, Canadian Journal of Chemistry, Vol. 51, page 466 (1973); Acton et al, Journal of Medicinal Chemistry, Vol. 17, No. 6, page 659 (1974); Kende et al, Journal of the American Chemical Society, Vol. 97, No. 15, page 4425 (1975) and Vol. 98, No. 7, page 1967 (1976); Sih et al, Tetrahedron Letters, page 3385 (1976); Swenton et al, Tetrahedron Letters, page 2383 (1977); and Kelly et al, Journal of the American Chemical Society, Vol. 99, page 5518 (1977). None of the known techniques for the total synthesis of anthracycline antibiotics such as doxorubicin have yet been proven to be commercially successful. Because of the demand for, and scarcity of, these compounds, a suitable synthesis technique is highly desired.

The present invention provides a practical technique for synthesizing doxorubicin and related compounds, from a readily available and inexpensive starting material. Specifically, in accordance with the present invention, doxorubicin and similar compounds may be synthesized from aloe-emodin. In addition, the present invention provides valuable intermediates useful in synthesizing doxorubicin and related compounds.

SUMMARY OF THE INVENTION

In accordance with the present invention, doxorubicin and its aglycone, adriamycinone, as well as other related compounds, may be synthesized from aloe-emodin by first halogenating aloe-emodin to produce 1,8-dihydroxy-3-halomethyl-9,10-anthraquinone. This compound is reacted with a dialkyl-2-carbalkoxysuccinate (in which the alkyl and alkoxy groups contain up to about 6 carbon atoms) to obtain 1,8-dihydroxy-3-(2,2,3-trialkoxycarbonylpropyl)-9,10-anthraquinone.

The ester groups of 1,8-dihydroxy-3-(2,2,3-trialkoxycarbonylpropyl)-9,10-anthraquinone are saponified to carboxy groups, yielding 1,8-dihydroxy-3-(2,2,3-tricarboxypropyl)-9,10-anthraquinone which is in turn decarboxylated to 1,8 dihydroxy-3-(2,3-dicarboxypropyl)-9,10-anthraquinone. The dicarboxy anthraquinone compound is subsequently reduced to 1,8 dihydroxy-3-(2,3-dicarboxypropyl)-9,10-(H)-anthr-9-one.

A cyclized product is prepared by condensing 1,8-dihydroxy-3-(2,3-dicarboxypropyl)-9,10-(H)-anthr-9-one to 6,8 dihydroxy-1,2,3,4,7,12-hexahydro-1,7 dioxo-[1,2]-benzanthracene-3-carboxylic acid. The cyclized benzanthracene compound is oxidized in two stages to produce 1,4,5-trihydroxy-2-(2,3-dicarboxypropyl)-9,10-anthraquinone. The trihydroxy anthraquinone compound is cyclized by reducing to 1,4,8-trihydroxy-3-(2,3-dicarboxypropyl)-9,10-(H)-anthr-9-one and then condensing to 5,7,12 trihydroxy-1,2,3,4,6,11-hexahydro-4,6-dioxonaphthacene-2-carboxylic acids. This acid is then oxidized to 5,7,12-trihydroxy-1,2,3,4,6,11-hexahydro-4,6,11-trioxo-naphthacene-2-carboxylic acid.

Reduction under hydrogenolysis conditions leads to 5,7,12-trihydroxy-1,2,3,4,6,11-hexahydro-6,11-dioxonaphthacene-2-carboxylic acid. This compound is reacted with methyl lithium to produce 2-methylcarbonyl-5,7,12-trihydroxy-1,2,3,4,6,11-hexahydro-6,11-dioxonaphthacene.

Those skilled in the art will recognize that there are many potentially attractive routes to daunomycin-doxorubicin-carminomycin and their analogs from this intermediate. The preferred embodiment of the present invention, however, leads efficiently to intermediates of well-established synthetic utility by the following technique. By Baeyer-Villiger oxidation 2-methylcarbonyl-5,7,12-trihydroxy-1,2,3,4,6,11-hexahydro-6,11-dioxonaphthacene is converted to 5,7,12-trihydroxy-2-acetoxy-1,2,3,4,6,11-hexahydro-6,11-dioxonaphthacene. Hydrolysis of this compound produces 2,5,7,12-tetrahydroxy-1,2,3,4,6,11-hexahydro-6,11-dioxonaphthacene.

The tetrahydroxy dioxonaphthacene compound may be oxidized to produce 5,7,12-trihydroxy-1,2,3,4,6,11-hexahydro-2,6,11-trioxonaphthacene. This latter compound may be converted to carminomycinone, using the technique described in Kende et al, Journal of the American Chemical Society, Vol. 98, no. 7, p. 1967 (1976) for converting 5,12-dihydroxy-7-methoxy-1,2,3,4,6,11-hexahydro-2,6,11-trioxonaphthacene to daunomycinone. Carminomycinone can be converted to carminomycin using known techniques for converting the aglycone to the L-daunosamine glycoside. Suitable techniques include those disclosed in Arcamone et al, Chim. Ind. (Milan), Vol. 51, p. 834 (1969); U.S. Pat. No. 3,803,124; Acton et al, Journal of Medicinal Chemistry, Vol. 17, no. 6, p. 659 (1974); and Smith et al, Journal of the American Chemical Society, Vol. 98, no. 7, p. 1969 (1976).

The sequence of reactions described above also can be used to produce 5,12-dihydroxy-7-methoxy-1,2,3,4,6,11-hexahydro-2,6,11-trioxonaphthacene by merely using the 8-monomethyl ether of aloe-emodin, rather than aloe-emodin, as the starting material. The process of the present invention, unlike the process for producing this compound disclosed in Kende et al, supra, does not result in the formation of isomers which must be separated from the reaction mixture.

Of course, 5,12-dihydroxy-7-methoxy-1,2,3,4,6,11-hexahydro-2,6,11-trioxonaphthacene may be converted to daunomycinone following the technique disclosed in Kende et al, supra. Conversion of daunomycinone to adriamycinone and conversion of these aglycones to daunomycin and doxorubicin may be accomplished using techniques disclosed in the various publications cited above.

The present invention also provides valuable intermediates useful in preparing doxorubicin, and related compounds, including those having the formulas:

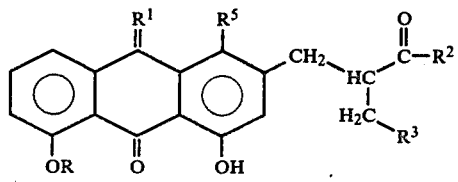
A.

wherein:
R is H or $R^4$;
$R^1$ is O or $H_2$;
$R^2$ is OH or $OR^4$;
$R^3$ is COOH or $COOR_4$;
$R^4$ is a $C_1$ to $C_6$ alkyl group; and
$R^5$ is H or OH.

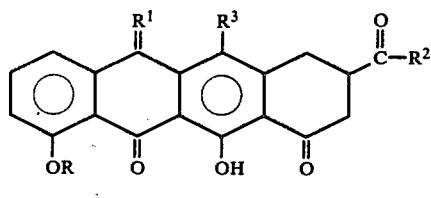
B.

wherein:
R is H or $R^4$;
$R^1$ is O or $H_2$;
$R^2$ is $CH_3$, OH, or $OR^4$;
$R^3$ is H or OH; and
$R^4$ is a $C_1$ to $C_6$ alkyl group.

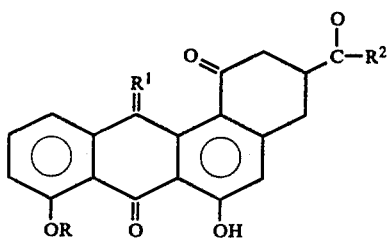
C.

wherein:
R is H or $R^3$;
$R^1$ is O or $H_2$;
$R^2$ is OH or $OR^3$;
$R^3$ is a $C_1$ to $C_6$ alkyl group.

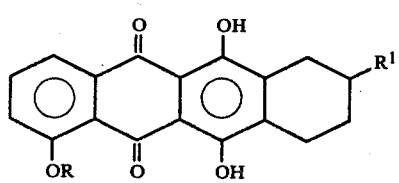
D.

wherein:
R is H or $R^2$;
$R^1$ is COOH, $COOR^2$, $COCH_3$, $OCOCH_3$, or OH; and
$R^2$ is a $C_1$ to $C_6$ alkyl group.

DESCRIPTION OF THE PREFERRED EMBODIMENTS

In the synthesis of the present invention, the starting material, aloe-emodin, may be obtained from any convenient source. For example, aloe-emodin may be isolated from naturally occurring species of aloe by water extraction of aloin followed by ferric chloride oxidation to cleave the glycosidically bound anthrone. Aloe-emodin has the formula:

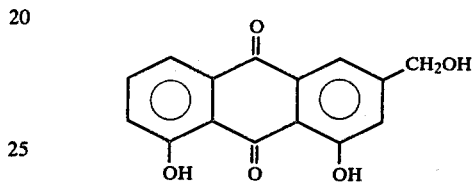
1.

Aloe-emodin is first halogenated, using any convenient halogenation technique, to yield 1,8-dihydroxy-3-halomethyl-9,10-anthraquinone having the formula:

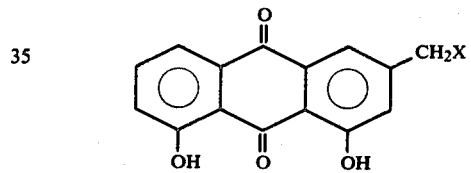
2.

Halogenation can be effected by, e.g., refluxing aloe-emodin with hydrobromic acid to obtain a brominated precipitate which may be washed and recovered. Halogenation can also be effected with a thionyl halide reagent.

The halogenated anthraquinone is next reacted with a dialkyl-2-carbalkoxysuccinate having the formula:

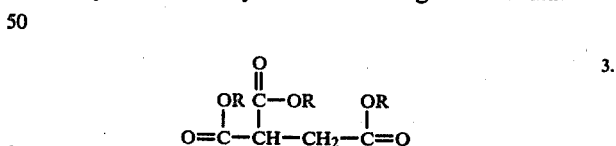
3.

in which R is an alkyl group of from 1 to 6 carbon atoms. A suitable dialkyl-2-carbalkoxysuccinate, diethyl-2-carbethoxysuccinate, can be prepared by reacting diethylmalonate with ethyl bromoacetate.

Reaction of the halogenated anthraquinone with a dialkyl-2-carbalkoxysuccinate can conveniently be carried out in an organic solvent in the presence of an alkali metal hydride. From the reaction solution may be recovered a 1,8-dihydroxy-3-(2,2,3-trialkoxycarbonylpropyl)-9,10-anthraquinone having the formula:

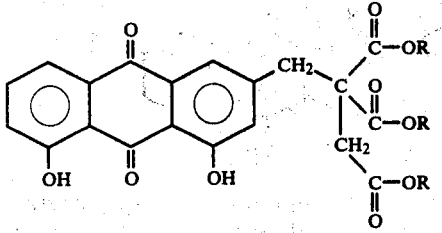

4.

where R is an alkyl group of from 1 to 6 carbon atoms.

The triester compounds of formula 4 are converted to tricarboxy compounds, preferably by reacting with a strong base such as sodium hydroxide or potassium hydroxide. The reaction results in the formation of 1,8-dihydroxy-3-(2,2,3-tricarboxypropyl)-9,10-anthraquinone having the formula:

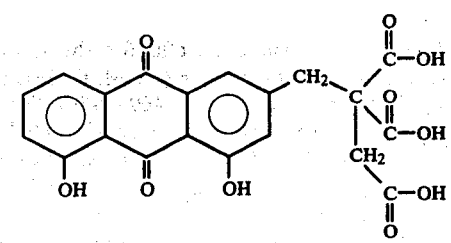

5.

The polycarboxylic acid of formula 5 is decarboxylated, e.g., by refluxing in an organic solvent in the presence of a strong acid to yield 1,8-dihydroxy-3-(2,3-dicarboxypropyl)-9,10-anthraquinone having the formula:

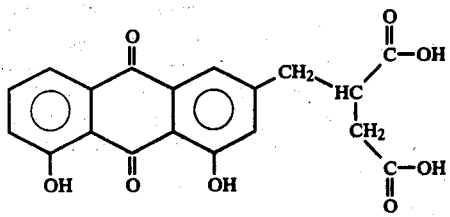

6.

The dicarboxylic compound of formula 6 is reduced, as by treating with a reducing agent such as stannous chloride or sodium borohydride, to produce 1,8-dihydroxy-3-(2,3-dicarboxypropyl)-9,10-(H)-anthr-9-one having the formula:

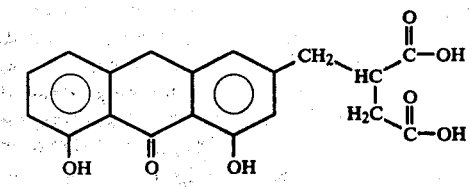

7.

The carboxylic acid anthrone of formula 7 is condensed, as by treating with a condensation catalyst such as hydrogen fluoride, to affect cyclization to the compound 6,8-dihydroxy-1,2,3,4,7,12-hexahydro-1,7 dioxy-(1,2)-benzanthracene-3-carboxylic acid having the formula:

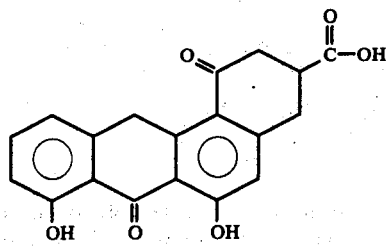

8.

The angular benzanthracene compound of formula 8 for oxidized by air in aqueous base, for example, KOH, solution to the compound 6,8-dihydroxy-1,2,3,4,7,12-hexahydro-1,7,12-trioxo-(1,2)-benzanthrancene-3-carboxylic acid having the formula:

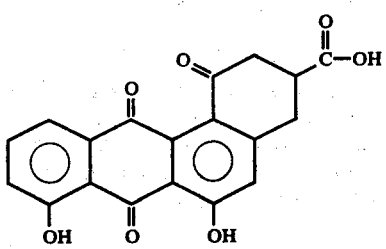

9.

Hydroxylation is achieved uniquely in the desired position by Baeyer-Villiger oxidation to produce 1,4,5-trihydroxy-2-(2,3-dicarboxypropyl)-9,10-anthraquinone having the formula:

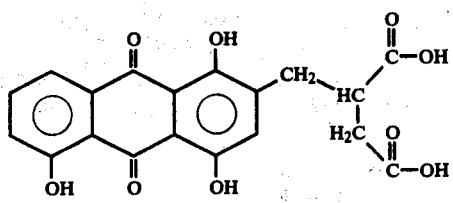

10.

The trihydroxyanthraquinone derivative of formula 10 is reduced, as by treating with a reducing agent such as stannous chloride or sodium borohydride, to produce, 1,4,8-trihydroxy-3-(2,3-dicarboxypropyl)-9,10-(H)-anthr-9-one having the following formula:

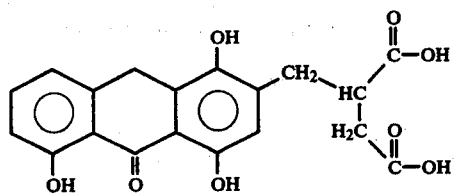

11.

Cyclization to the desired naphthacene structure is achieved by use of a condensation catalyst such as hydrogen fluoride, polyphosphoric acid or the like to produce 5,7,12-trihydroxy-1,2,3,4,6,11-hexahydro-4,6-dioxonaphthacene-2-carboxylic acid of the following formula:

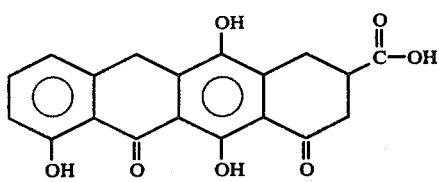

Air oxidation of a solution of the compound of formula 12 produces 5,7,12-trihydroxy-1,2,3,4,6,11-hexahydro-4,6,11-trioxonaphthacene-2-carboxylic acid of the formula:

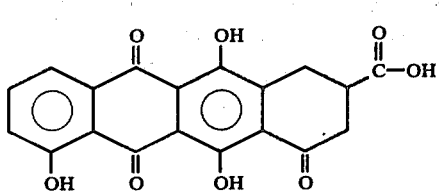

Hydrogenation using palladium on barium sulfate catalyst, removal of the catalyst by filtration and aeration of an alkaline solution yields 5,7,12-trihydroxy-1,2,3,4,6,11-hexahydro-6,11-dioxonaphthacene-2-carboxylic acid of the following formula:

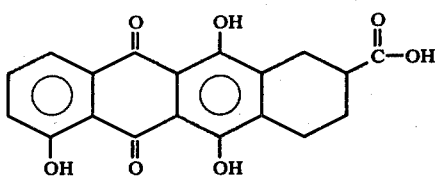

Reaction of the dioxonaphthacene of formula 14 with 5 molar equivalents of methyl lithium produces 2-methylcarbonyl-5,7,12-trihydroxy-1,2,3,4,6,11-hexahydro-6,11-dioxonaphthacene of the following formula:

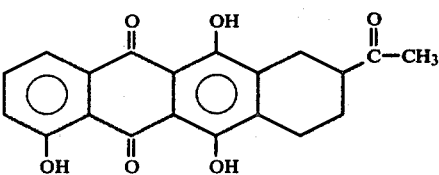

Oxidation of the compound of formula 15 with peracids under the conditions of the Baeyer-Villiger reaction produces 5,7,12-trihydroxy-2-acetoxy-1,2,3,4,6,11-hexahydro-6,11-dioxonaphthacene of the following formula:

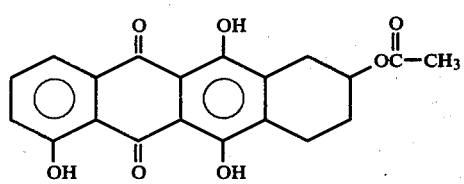

Hydrolysis of the acetoxy dioxonaphthacene compound results in the formation of 2,5,7,12-tetrahydroxy-1,2,3,4,6,11-hexahydro-6,11-dioxonaphthacene of the following formula:

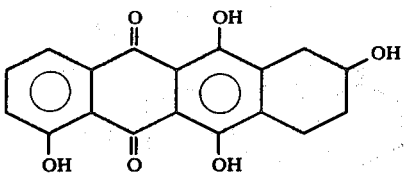

The tetrahydroxy dioxonaphthacene derivative of formula 17 may be oxidized to produce 5,7,12-trihydroxy-1,2,3,4,6,11-hexahydro-2,6,11-trioxonaphthacene of the following formula:

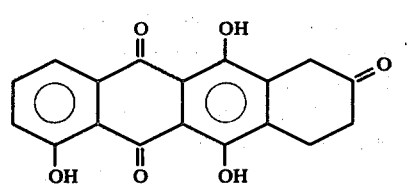

This substance is a synthon useful for the direct chemical synthesis of carminomycin (see M. G. Brazhnikova et al., J. Antibiotics, 29, page 469 (1976), G. R. Pettit et al., J. Am. Chem. Soc., 97, page 7387 (1975) and M. C. Wani et al., ibid., 5955 (1975)) by an obvious adaptation of the methods of Kende et al., J. Am Chem. Soc., 98, page 1967 (1976).

The method of the present invention can be used for the direct chemical synthesis of doxorubicin-daunomycin by using the 8-monomethyl ether of aloe-emodin as the starting material and following the above reacted sequence of reactions. The necessary monomethylemodin can be prepared conveniently by the following reactions.

Methylation of aloe-emodin with dimethylsulfate and potassium carbonate in organic reaction-inert solvents can be stopped at the monomethyl ether stage. It has been found most convenient, on a large scale, to acetylate the monomethyl ether mixture, and separate the isomers by fractional crystallization. Saponification produces the 8-monomethylether of aloe-emodin of the following formula:

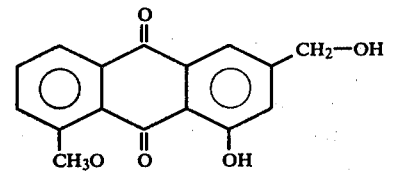

Alternately, the diacetate of aloe-emodin can be made through the use of boroacetic anhydride. Methylation of the remaining free phenolic hydroxyl group and saponification produces the monomethyl ether of formula 19. Obviously it is possible to introduce other lower alkoxy groups at the 8 position in a similar manner by merely using other alkyl groups containing reactants in place of dimethylsulfate, etc.

Repetition of the same reaction sequence previously described using the 8-monomethyl ether of aloe-emodin, rather than aloe-emodin, results in the production of the known daunomycin/adriamycin synthon, 2,5,12-trihydroxy-7-methoxy-1,2,3,4,6,11-hexahydro-6,11-dioxonaphthacene, having the following formula:

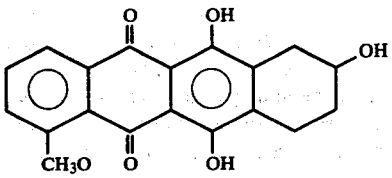

20.

Compound 20 is analogous to compound 17 and is readily oxidized by the method of Lee et al., J. Org. Chem., 41, page 2296 (1976) to the established synthon (Kende et al., J. Am. Chem. Soc., 98, p. 1967 (1976)) 5,12-dihydroxy-7-methoxy-1,2,3,4,6,11-hexahydro-2,6,11-trioxonaphthacene of the following formula:

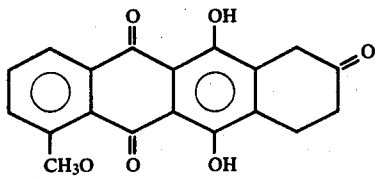

21.

The process of the present invention, previously described, results in the formation of a number of useful intermediates. Particularly useful intermediates are those having the formula:

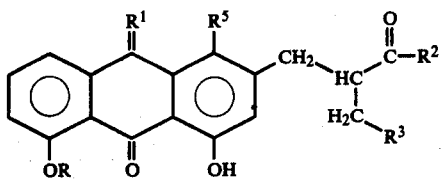

A.

wherein:
R is H or $R^4$;
$R^1$ is O or $H_2$;
$R^2$ is OH or $OR^4$;
$R^3$ is COOH or $COOR^4$;
$R^4$ is a $C_1$ to $C_6$ alkyl group; and
$R^5$ is H or OH.

Examples of intermediates corresponding to the above-identified formula include (a) 1,8 dihydroxy-3-(2,3-dicarboxypropyl)-9,10-anthraquinone (the compounds of formula 6) where R is hydrogen, $R^1$ is oxygen, $R^2$ is OH, $R^3$ is COOH, and $R^5$ is H; (b) 1,8-dihydroxy-3-(2,3-dicarboxypropyl)-9,10-(H)-anthr-9-one (the compound of formula 7) where R is hydrogen, $R^1$ is $H_2$, $R^2$ is OH, $R^3$ is COOH, and $R^5$ is H; and (c) 1,4,5-trihydroxy-2-(2,3,-dicarboxypropyl)-9,10-anthraquinone (the compound of formula 10) where R is hydrogen, $R^1$ is oxygen, $R^2$ is OH, $R^3$ is COOH, and $R^5$ is OH. This latter compound may readily be converted to 1,4,5-trihydroxy-2(2,3-dicarboxypropyl)-9,10-(H)-anthr-9-one ($R^1$ equals $H_2$) by reducing with a reducing agent such as sodium borohydride.

Compounds corresponding to the above formula in which R is $R^4$ (a lower alkyl group), $R^2$ is $OR^4$, $R^3$ is $COOR^4$, $R^5$ is OH, and $R^1$ is oxygen may be prepared by reacting the compound of formula 10 with alkyl halides. Similarly, compounds in which R is $R^4$, $R^2$ is $OR^4$, $R^3$ is $COOR^4$, $R^1$ is O or $H_2$ and $R^5$ is H can be prepared by reacting the compounds of formulas 6 or 7 with alkyl halides. Compounds corresponding to the above formula in which R is $R^4$ (a lower alkyl group), $R^2$ and $R^5$ are OH or $OR^4$, $R^3$ is COOR and $R^1$ is oxygen also may be prepared directly by starting the reaction sequence with an aloe-emodin monoalkyl ether, such as an aloe-emodin monomethyl ether.

Other useful intermediates correspond to the formula:

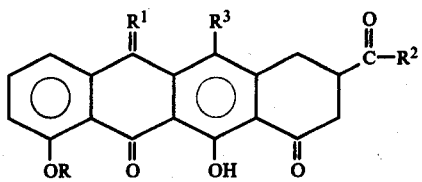

B.

wherein:
R is H or $R^4$;
$R^1$ is O or $H_2$;
$R^2$ is $CH_3$, OH, or $OR^4$;
$R^3$ is H or OH; and
$R^4$ is a $C_1$ to $C_6$ alkyl group.

Examples of intermediates corresponding to the above formula include (a) 5,7,12-trihydroxy-1,2,3,4,6,11-hexahydro 4,6,11-trioxonaphthacene-2-carboxylic acid (the compound of formula 13) where R is H, $R^1$ is oxygen, and $R^2$ and $R^3$ are OH, (b) its anthrone (the compound of formula 12) where R is H, $R^1$ is $H_2$, and $R^2$ and $R^3$ are OH, and (c) 7-methoxy-5,12-dihydroxy-1,2,3,4,6,11-hexahydro-4,6,11-trioxonaphthacene-2-carboxylic acid, where R is $CH_3$ $R^1$ is $H_2$, and $R^2$ and $R^3$ are OH. Preferably in the above formula $R^1$ is not $H_2$ when $R^3$ is H.

Additional useful intermediates correspond to the formula:

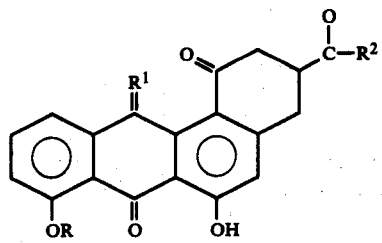

C.

wherein:
R is H or $R^3$;
$R^1$ is O or $H_2$;
$R^2$ is OH or $OR^3$;
$R^3$ is a $C_1$ to $C_6$ alkyl group.

Examples of intermediates corresponding to the above identified formula include 6,8-dihydroxy-1,2,3,4,7,12-hexahydro-1,7 dioxy-[1,2]-benzanthracene-3-carboxylic acid (the compound of formula 8) where R and $R^3$ are H, $R^1$ is $H_2$ and $R^2$ is OH and 6,8-dihydroxy-1,2,3,4,7,12-heptahydro-1,7,12-trioxo-[1,2]-benzanthracene-3-carboxylic acid (the compound of formula 9) where R and $R^3$ are H, $R^1$ is O and $R^2$ is OH.

Compounds corresponding to the following formula are also useful intermediates:

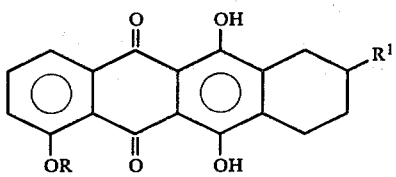

wherein:
R is H or $R^2$;
$R^1$ is COOH, $COOR^2$, $COCH_3$, $OCOCH_3$, or OH; and
$R^2$ is $C_1$ to $C_6$ alkyl group.

Examples of intermediates corresponding to the above formula include: (a) 5,7,12-trihydroxy-1,2,3,4,6,11-hexahydro-6,11-dioxonaphthacene-2-carboxylic acid (the compound of formula 14) where R=H and $R^1$=COOH; (b) 7-methoxy-5,12-dihydroxy-1,2,3,4,6,11-hexahydro-6,11-dioxonaphthacene-2-carboxylic acid where R=$CH_3$ and $R^1$=COOH; (c) 5,7,12-trihydroxy-1,2,3,4,6,11-hexahydro-2-methylcarbonyl-6,11-dioxonaphthacene (the compound of formula 15) where R=H and $R^1$=$COCH_3$; (d) 7-methoxy-5,12-dihydroxy-1,2,3,4,6,11-hexahydro-2-methylcarbonyl-6,11-dioxonaphthacene where R=$CH_3$ and $R^1$=$COCH_3$; (e) 2-acetoxy-5,7,12-trihydroxy-1,2,3,4,6,11-hexahydro-6,11-dioxonaphthacene (the compound of formula 16) where R=H and $R^1$=$OCOCH_3$; (f) 2-acetoxy-7-methoxy-5,12-dihydroxy-1,2,3,4,6,11-hexahydro-6,11-dioxonaphthacene where R=$CH_3$ and $R^1$=$OCOCH_3$; and (g) 2,5,7,12-tetrahydroxy-1,2,3,4,6,11-hexahydro-6,11-dioxonaphthacene (the compound of formula 17) where R=H and $R^1$=OH.

The following examples further illustrate preferred embodiments of the present invention. The examples should in no way be considered limiting, but are merely illustrative of the various features of the present invention.

EXAMPLE 1

This example demonstrates the preparation of aloe emodin from Cape Aloes. Cape Aloes (1 kg.) is macerated with 3 liters of tap water at room temperature, using a plastic bucket as container. The water is carefully filtered by suction directly into a 5 liter flask keeping as much of the sticky resin as possible in the bucket. The resin is macerated with more water (about 1 liter) and this suspension is poured into the flask by filtration. The combined filtrates are then treated with ferric chloride hexahydrate (2 lb; 912 g) and the mixture is heated at 95°–98° C. for six hours. The cooled reaction mixture is filtered and the dark residue so obtained is dried under vacuum at 100° C. (approximately 230 g may be expected).

The dark solid is then dispersed in ethyl acetate (1 liter) with the aid of a high torque stirrer (Dispex 45 is suitable). The suspension is poured into a 5 liter flask and more ethyl acetate is added (3 liters). The suspension is refluxed for 10 minutes and then is filtered under vacuum. The filtrate is treated with charcoal (50 g) and then refluxed for 5 minutes with stirring. The suspension is filtered through a celite pad and the filtrate is concentrated to 300 ml. The resulting aloe-emodin is filtered off. Approximately 16 g are recovered.

Additional aloe-emodin may be recovered from the dark residue left from the first ethyl acetate extraction by extracting again with fresh solvent, e.g., four liters, and treating the filtrate with 10 g of activated charcoal. This suspension is then filtered through the same celite pad as was used previously and concentrated as before. If desired, the ethyl acetate extraction procedure is repeated once or twice more to recover additional aloe-emodin.

EXAMPLE 2

1,8-Dihydroxy-3-bromomethyl-9,10-anthraquinone (formula 2, in which X is Br) may be prepared as follows. A suspension of aloe-emodin (5 g) in 48% hydrobromic acid is refluxed for 2 hours to afford a precipitate. The precipitate is filtered to afford a crystalline solid which is extracted with $CHCl_3$. The extract is washed with saturated NaCl solution, dried over $Na_2SO_4$, and then evaporated till about 3/5 of its volume, producing a precipitate, which is filtered to give bright orange needles (5.4 g). Recrystallization from $CHCl_3$ gives bright orange-yellow needles having a m.p. of 217°–219° C.

EXAMPLE 3

1,8-Dihydroxy-3-chloromethyl-9,10-anthraquinone (formula 2, in which X is Cl) may be prepared by adding thionyl chloride (3.7 mM) to a stirred suspension of aloe-emodin. (1.85 mM) in dichloroethane (30 ml). Pyridine (about 16 drops) was added to start the reaction. The starting material dissolved and after about 1 hour the product began to crystallize from the reaction mixture. After 3 hours, the reaction mixture was evaporated to give a solid residue. This was suspended in water and filtered to give 0.56 g (100% yield) of a product having a m.p. of 165°–170° C. Recrystallization from acetic acid gave a pure sample having a m.p. of 175°–176° C.

EXAMPLE 4

Diethyl-2-carbethoxysuccinate (formula 3, in which R are ethyl groups) is prepared by dissolving ethyl malonate (66 g, 0.5 moles) in tetrahydrofuran (500 ml). Sodium hydride (19.7 g of a 66% suspension in oil) (0.5 mole) is washed twice with petroleum ether. (b.p. 30°–66°) and added to the stirred solution in small portions. Ethyl bromoacetate (83.5 g, 0.5 moles) is then added slowly from a dropping funnel. After stirring for 16 hours, the resultant white suspension is transferred to a separatory funnel along with a saturated aqueous sodium chloride solution (1 liter) and dichloroethane (1 liter). After shaking and separating the layers, the water layer is extracted with two additional liter portions of dichloroethane. The combined organic layers are dried over sodium sulfate before filtration and evaporation. The crude product is distilled under reduced pressure and the fractions boiling at 105°–112° at 2.5 mm Hg (12 ml) and 112°–115° (25 ml) are kept for use in the reaction of the next example.

EXAMPLE 5

To a stirring solution of diethyl-2-carbethoxysuccinate (15 g) prepared in accordance with Example 4, in dimethyl formamide (30 ml), 64% NaH (2.6 g) is added incrementally under cooling with ice-water. The mixture is stirred at room temperature for 20 minutes, followed by adding a solution of 1,8-dihydroxy-3-bromomethyl-9,10-anthraquinone (9.6 g), prepared in accordance with Example 2, and 64% NaH (2.6 g) in dimethyl formamide (300 ml). The mixture is stirred for 30 minutes and then heated up to 70° C. Stirring is continued for an additional 3 hours at 70° C. and the mixture is stirred for several hours, e.g., overnight, at room temperature. The mixture is poured into water (about 1 liter), acidified with concentrated HCl, and then extracted with benzene. The extract is washed with a saturated NaCl solution, and then evaporated to leave a dark brown syrup, which was subjected to chromatography on silica gel (200 g). Elution with benzene—CHCl$_3$ (2:1 V/V) affords bright orange crystals (12 g), whose recrystallization from MeOH gives the desired 1,8-dihydroxy-3-(2,2,3-triethoxycarbonylpropyl)-9,10-anthraquinone (formula 4, in which the R groups are ethyl radicals) as bright orange plates, having a m.p. of 89°–90°.

EXAMPLE 6

A mixture of the 1,8-dihydroxy-3(2,2,3-triethoxycarbonylpropyl)-9,10-anthraquinone (2 g) of Example 5, KOH (2 g), H$_2$O (15 ml) and EtOH (50 ml) is refluxed using an oil bath. After evaporation of EtOH, H$_2$O is added to the residue which is then acidified with concentrated HCl. A viscous syrup separates which is triturated with a spatula and cooled with ice and H$_2$O, to afford a yellow crystalline solid. The yellow solid is recovered by filtration to give 1.8 grams of a product shown by subsequent analysis to be 1,8-dihydroxy-3-(2,2,3-tricarboxypropyl)-9,10-anthraquinone (formula 5).

EXAMPLE 7

A suspension of 1,8-dihydroxy-3-(2,2,3-tricarboxypropyl)-9,10-anthraquinone (6 g), such as prepared by the technique of Example 6, in concentrated HCl (50 ml), H$_2$O (50 ml) and diglyme (150 ml) is refluxed for 18 hours in an oil bath. The solvent is evaporated in vacuum to leave a residue. Addition of an excess of H$_2$O leaves a crystalline powder, which is filtered to yield 5.26 grams of a product. Characterization of the product shows it to be 1,8-dihydroxy-3-(2,3-dicarboxypropyl)-9,10-anthraquinone (formula 6).

EXAMPLE 8

A mixture of 3.7 grams of 1,8-dihydroxy-3-(2,3-dicarboxylpropyl)-9,10-anthraquinone of Example 7, stannous chloride (4.51 g), concentrated HCl (20 ml) and acetic acid (80 ml) is heated at 120° for 1 hour with stirring in an oil bath. Subsequently, H$_2$O (60 ml) is added to the reaction mixture to afford a precipitate which is filtered and washed with water to afford a yellow-green crystalline solid (2.9 g) product.

The mother liquor is extracted with ethyl ether, washed with saturated NaCl solution, dried over Na$_2$SO$_4$, and evaporated to leave a residue. The residue is filtered (washing with H$_2$O) to afford additional yellow-green solid (700 mg) product. Characterization shows the product to be 1,8-dihydroxy-3-(2,3-dicarboxypropyl)-9,10-(H)-anthr-9-one (formula 7).

Alternatively, the reduction of the product of Example 7 can be achieved using sodium borohydride rather than stannous chloride.

EXAMPLE 9

100 mg of the diacid anthrone of Example 8 was placed in a Paar bomb with liquid HF (10 ml) and heated at 55°–60° C. for three hours. The bomb was cooled, opened, and the HF was allowed to evaporate at room temperature. The resulting residue was triturated with water and filtered to yield 94.5 mg of a crude red-violet crystalline solid product. The product, 6,8-dihydroxy-1,2,3,4,7,12-hexahydro-1,7-dioxo-[1,2]-benzanthracene-3-carboxylic acid (formula 8), because of instability, was subject to the reaction of the next example, without purification.

EXAMPLE 10

The total product of Example 9 was dissolved in 50 ml of methanol containing 200 mg of potassium hydroxide and allowed to stand for 4 hours at room temperature. Acidification with dilute hydrochloric acid led to the precipitation of orange-red 6,8-dihydroxy-1,2,3,4,7,12-hexahydro-1,7,12-trioxo-(1,2)-benzanthracene-3-carboxylic acid (formula 9).

EXAMPLE 11

A suspension of 94.5 mg of the crude cyclized compound of Example 10 in a mixture of acetic acid (2 ml), 31.5% H$_2$O$_2$ (0.5 ml) and concentrated H$_2$SO$_4$ (3 drops) was stirred for 5 days at room temperature. An excess of H$_2$O was added to the above mixture to give a precipitate. The precipitate was filtered to afford a brownish crystalline solid, which was extracted with ethyl acetate. The extract was washed with saturated NaCl solution, dried over Na$_2$SO$_4$, and then evaporated to leave a brown crystalline solid (77.3 mg). Characterization of a methylated derivative of the solid shows the solid to be 1,4,5-trihydroxy-2-(2,3-dicarboxypropyl)-9,10-anthraquinone (formula 10). The methyl derivative is made in accordance with Example 12.

EXAMPLE 12

A suspended solution of the crude dicarboxylic acid of Example 10 (77 mg) in MeOH (15 ml) was refluxed with stirring while passing in HCl gas for 3 hours. The solvent was evaporated to leave a residue which was extracted with CHCl$_3$. The extract was washed with saturated NaCl solution, dried over Na$_2$SO$_4$, and then evaporated to leave a red-brown syrup, which was subjected to chromatography on silica gel (5 g). Elution with CHCl$_3$ afforded 37.7 mg of a bright orange solid which was filtered and washed with MeOH, to give a red-brown crystalline solid. Recrystallization from MeOH-CHCl$_3$ gave 1,4,5-trihydroxy-2-(2,3-dimethoxycarbonylpropyl)-9,10-anthraquinone (formula A in which R is H, R$^1$ is O, R$^2$ is OCH$_3$, R$^3$ is COOCH$_3$, and R$^5$ is OH).

EXAMPLE 13

To a stirring solution of the dicarboxylic acid of Example 10 (85 mg) in MeOH (40 ml) and CHCl$_3$ (10 ml), NaBH$_4$ (120 mg) was incrementally added at room temperature under N$_2$. The mixture was stirred for an additional 4 hours under the same conditions. The solvent was evaporated at room temperature to leave a residue to which H$_2$O was added and the mixture was acidified with concentrated HCl and extracted with CHCl$_3$. The extract was washed with a saturated NaCl solution, dried over Na$_2$SO$_4$, and evaporated to leave a brown-red crystalline syrup. The syrup was subjected to chromatography on silica gel (20 g). Elution with CHCl$_3$ afforded brown crystals (38 mg) and recrystallization from MeOH gave a brown powder.

Analysis of the product showed it to be 1,4,5-trihydroxy-2(2,3-dicarboxypropyl)-9,10(H)-anthr-9-one (formula 11).

EXAMPLE 14

A suspension of the ester prepared in accordance with Example 12 (200 mg), silver oxide (700 mg) and methyl iodide (700 mg) in dimethylformamide (15 ml) was stirred in the dark for 16 hours at which time an equal fresh quantity of silver oxide and methyl iodide was added. After stirring for 16 hours more, the suspension was evaporated to leave a residue, which was triturated with benzene and the solution was filtered through celite. The combined benzene filtrates were evaporated to leave a brown syrup (200 mg), which was chromatographed on silica gel (2×27 cm). Elution with $CHCl_3$ ethyl acetate (5:1 V/V) gave a rather pure compound (50 mg) and an additional less pure compound (40 mg). The less pure material was separated on preparative thick layer chromatography (solvent system $CHCl_3$: MeOH 9.5:0.5 V/V) to give a brown-yellow syrup.

Analysis of the recovered products showed them to be 1,4,5-trimethoxy-2-(2,3-dimethoxycarbonylpropyl)-9,10-anthraquinone (formula A where R is $CH_3$, $R^1$ is O, $R^2$ is $OCH_3$, $R^3$ is $COOCH_3$, and $R^5$ is $OCH_3$.

EXAMPLE 15

A mixture of the dimethylester of Example 14 (19.5 mg), KOH (100 mg), $H_2O$ (1 ml) and ethanol (5 ml) was refluxed for 3.5 hours in oil bath. The solvent was evaporated to leave a residue which was covered with concentrated HCl solution and extracted with $CHCl_3$. The extract was washed with saturated NaCl solution, dried over $Na_2SO_4$, and evaporated to leave a yellow syrup (14 mg).

Analysis of the yellow syrup showed it to be 1,4,5-trimethoxy-2-(2,3-dicarboxypropyl)-9,10-anthraquinone (formula A in which R is $CH_3$, $R^1$ is O, $R^2$ is OH, $R^3$ is COOH, and $R^5$ is $OCH_3$).

EXAMPLE 16

The trihydroxydicarboxylic acid anthrone of Example 13 (25 mg) was placed in a Parr bomb with liquid hydrogen fluoride (20 ml) and heated at 70° for 6.5 hr. on a water bath under a nitrogen atmosphere. The bomb was cooled and opened and the HF was removed by a stream of nitrogen. The residue containing crude compound of formula 12 was extracted with a mixture of ethyl acetate and methanol and the extracts were washed with saturated salt solution and evaporated to a green-brown solid (28 mg) which was resolved by chromatography on silica gel (chloroform/methanol elution) to give a brown-red powder as the major component. Mass spectral and ultraviolet analysis of this unstable product showed it to be 5,7,12-trihydroxy-1,2,3,4,6,11-hexahydro-4,6,11-trioxonaphthacene-2-carboxylic acid (formula 13). This compound can be more fully characterized as its methyl ester acetate derivative.

EXAMPLE 17

The naphthaceneone of Example 16 (50 mg) was dissolved in dioxane (75 ml) and this was added to a stirring suspension of pre-reduced 5% palladium on barium sulfate catalyst in a hydrogen atmosphere. When uptake of hydrogen ceased (about one hour), the catalyst was removed by filtration and the solvent removed by evaporation. The yellow-brown residue was dissolved in 5% sodium hydroxide solution and the intensely colored purple solution was allowed to stand for one hour before acidification and extraction into methylene chloride. Evaporation produced 30 mg of a reddish crystalline product which proved to be 5,7,12-trihydroxy-1,2,3,4,6,11-hexahydro-6,11-dioxonaphthacene-2-carboxylic acid (formula 14).

EXAMPLE 18

The naphthacenequinone carboxylic acid of Example 17 (100 mg) was dissolved in one liter of dry tetrahydrofuran and 5 molar equivalents of methyl lithium in diethyl ether were added. This was stirred at room temperature for 3 hours and then acidified with acetic acid before concentrating to about 50 ml volume. After dilution with water, the precipitated solids were filtered off and air dried to give 90 mg of crude 2-methylcarbonyl-5,7,12-trihydroxy-1,2,3,4,6,11-hexahydro-6,11-dioxonaphthacene (formula 15). Material pure enough for the next step could be prepared by chromatography in methanol over a column of Sephadex LH-20 adsorbant. The molecular formula was confirmed to be $C_{20}H_{16}O_6$ (352) by mass spectrometry.

EXAMPLE 19

A suspension of the methyl ketone of Example 18 (90 mg) in a mixture of acetic acid (2 ml), 31.5% $H_2O_2$ (0.5 ml) and concentrated $H_2SO_4$ (2 drops) was stirred overnight at room temperature. Water was added until precipitation of the product was complete and filtration produced 75 mg of reddish brown 5,7,12-trihydroxy-2-acetoxy-1,2,3,4,6,11-hexahydro-6,11-dioxonaphthacene (formula 16) (infrared maximum 1740 $cm^{-1}$).

EXAMPLE 20

The ester of Example 19 (50 mg) was suspended in a 1 N solution of hydrochloric acid in 1:1 aqueous methanol and this was heated for one hour on the steam bath. The excess solvent was removed by concentration on a hot plate and the suspension cooled and filtered to give 48 mg of 2,5,7,12-tetrahydroxy-1,2,3,4,6,11-hexahydro-6,11-dioxonaphthacene (formula 17) as a red powder.

EXAMPLE 21

The alcohol of Example 20 (35 mg) was treated with 130 mg of dicyclohexylcarbodiimide and 0.4 ml of trifluoroacetic acid and 3 ml of dimethyl sulfoxide for 3 hours and then extracted several times with benzene. Evaporation of the benzene layers produced brown-red 5,7,12-trihydroxy-1,2,3,4,6,11-hexahydro-2,6,11-trioxonaphthacene (formula 18), m.p. above 300° C., infrared maximum 1730 $cm^{-1}$).

EXAMPLE 22

To a suspension of 0.54 g aloe-emodin in 40 ml acetone and 20 ml dimethylformamide, 0.25 g dimethyl sulfate and 0.27 g potassium carbonate were added and the mixture refluxed for 16 hours. Another 0.25 g dimethyl sulfate and 0.27 g potassium carbonate were then added. The reaction was hastened by adding two drops of dry methanol and refluxing continued (three hours) until the disappearance of the starting material. The reaction mixture was cooled, diluted with 50 ml water and extracted with chloroform. The chloroform extract was washed with water (×3) and brine and evaporated to yield a dark reddish residue. This was redissolved in chloroform and boiled with charcoal and filtered. Evaporation of the filtrate furnished 0.45 g of yellow crystals of a mixture of monomethyl ethers of aloe-emodin mixed with small amount of dimethyl ether.

The mixture of monomethyl ethers of aloe-emodin obtained as above (0.8 g) was dissolved in pyridine (10 ml) and acetic anhydride (20 ml) was added and the mixture was left standing overnight at room temperature. The pyridine and acetic acid were distilled off in vacuum and the residue was triturated with water. The suspension of yellow solid was filtered and air dried (0.8 g). Crystallization from benzene afforded one of the diacetylmonomethylaloe-emodin isomers in practically pure form (0.123 g). Recrystallization from benzene furnished a pure sample which was proved to be 8-methoxy-3-acetoxymethyl-1-acetoxy anthraquinone, m.p. 186°-188°, ir (KBr) 3480, 1765, 1735, 1665, 1610 and 1590 cm-1. Anal. Calcd. for $C_{20}H_{14}O_7$: C, 65.57; H, 3.85, found: C, 65.54, H, 4.05.

EXAMPLE 23

The 8-methoxy-3-acetoxymethyl-1-acetoxy anthraquinone (120 mg) of Example 22 was refluxed in methanol (30 ml) with concentrated hydrochloric acid (10 ml) and water (10 ml) for three hours. The solvents and acid were evaporated off in vacuum and the residue crystallized from chloroform to obtain reddish yellow crystals (65 mg) of 1-hydroxy-3-hydroxymethyl-8-methoxy anthraquinone (formula 19). m.p. 215°-216°, ir (KBr) 3520-3460, 1670, 1635, 1585 cm-1.

EXAMPLE 24

Boric acid (5 g) was dissolved in acetic anhydride (100 ml) by heating on a steam bath for about half hour. Aloe-emodin (5 g) was added to it and heated on the steam bath for six hours and left standing overnight at room temperature. It was poured into water (ca. 300 ml) and warmed to hydrolyze the acetic anhydride. The mixture was then cooled in ice and the yellow solid that separated was filtered (6.3 g). Crystallization from chloroform-benzene-light petrol furnished 2.5 g of yellow crystals which was practically pure 1-hydroxy-3-acetoxymethyl-8-acetyl-anthraquinone. As this compound and its isomer are inseparable on TLC, the only means of identification is the NMR absorption at around 5.2 PPM (S).

The following physical data were obtained for 1-hydroxy-3-acetoxymethyl-8-acetylanthraquinone: m.p. 194°-196°; ir (KBr) 3450, 1772, 1740, 1680, 1635 and 1600 cm-1. The mother liquor on concentration and adding light petrol deposited 2.6 g of a yellowish black crystalline solid. NMR showed that it is the other isomer viz. 1-acetyl-3-acetoxymethyl-8-hydroxyanthraquinone. Repeated crystallization from chloroform-light petrol furnished the pure isomer, m.p. 190°-191°. ir (KBr) 3460, 1775, 1740, 1672, 1630 and 1607 cm-1.

The diacetate (2 g) was refluxed in acetone (100 ml) with dimethyl sulfate (2.5 g) and potassium carbonate (5 g) for 16 hours. The acetone was distilled off in vacuum and the residue was suspended in water. The brown precipitate was filtered off and washed with water. The precipitate weighed 2.2 g. On crystallization from benzene it afforded one crop of crystals weighing 0.8 g which was found to be identical with 1-methoxy-3-acetoxymethyl-8-acetylanthraquinone of Example 22 by TLC and NMR.

Although the present invention has been described in connection with preferred embodiments, it is understood that modifications and variations may be resorted to without departing from the spirit and scope of the invention. Such modifications are considered to be within the purview and scope of the invention and the appended claims.

What is claimed is:
1. A process for producing 5,7,12-trihydroxy-1,2,3,4,6,11-hexahydro-2,6,11-trioxonaphthacene from aloe-emodin comprising
  a. halogenating aloe-emodin to produce 1,8-dihydroxy-3-halomethyl-9,10-anthraquinone;
  b. reacting 1,8-dihydroxy-3-halomethyl-9,10-anthraquinone with a dialkyl-2-carbalkoxysuccinate in which the alkyl and alkoxy groups contain up to about 6 carbon atoms, to produce 1,8-dihydroxy-3-(2,2,3-trialkoxycarbonylpropyl)-9,10-anthraquinone;
  c. saponifying 1,8-dihydroxy-3-(2,2,3-trialkoxycarbonylpropyl)-9,10-anthraquinone to produce 1,8-dihydroxy-3-(2,2,3-tricarboxypropyl)-9,10-anthraquinone;
  d. decarboxylating 1,8-dihydroxy-3-(2,2,3-tricarboxypropyl)-9,10-anthraquinone to produce 1,8-dihydroxy-3-(2,3-dicarboxypropyl)-9,10-anthraquinone;
  e. reducing 1,8-dihydroxy-3-(2,3-dicarboxypropyl)-9,10-anthraquinone to 1,8 dihydroxy-3-(2,3-dicarboxypropyl)-9,10-(H)-anthr-9-one;
  f. cyclizing 1,8 dihydroxy-3-(2,3-dicarboxypropyl)-9,10-(H)-anthr-9-one to produce 6,8-dihydroxy-1,2,3,4,7,12-hexahydro-1,7-dioxo-[1,2]-benzanthracene-3-carboxylic acid;
  g. oxidizing 6,8 dihydroxy-1,2,3,4,7,12-hexahydro-1,7 dioxo-[1,2]-benzanthracene-3-carboxylic acid to produce 6,8-dihydroxy-1,2,3,4,7,12-hexahydro-1,7,12-trioxo-[1,2]-benzanthracene-3-carboxylic acid;
  h. subjecting 6,8-dihydroxy-1,2,3,4,7,12-hexahydro-1,7,12-trioxo-[1,2]-benzanthracene-3-carboxylic acid to Baeyer-Villiger oxidization to produce 1,4,5-trihydroxy-2-(2,3-dicarboxypropyl)-9,10-anthraquinone;
  i. reducing 1,4,5-trihydroxy-2-(2,3-dicarboxypropyl)-9,10-anthraquinone to produce 1,4,8-trihydroxy-3-(2,3-dicarboxypropyl)-9,10-(H)-anthr-9-one;
  j. condensing 1,4,8-trihydroxy-3-(2,3-dicarboxypropyl)-9,10-(H)-anthr-9-one to produce 5,7-12-trihydroxy-1,2,3,4,6,11-hexahydro-4,6-dioxonaphthacene-2-carboxylic acid;
  k. oxidizing 5,7,12-trihydroxy-1,2,3,4,6,11-hexahydro-4,6-dioxonaphthacene to produce 5,7,12-trihydroxy-1,2,3,4,6,11-hexahydro-4,6,11-trioxonaphthacene-2-carboxylic acid;
  l. reducing 5,7,12-trihydroxy-1,2,3,4,6,11-hexahydro-4,6,11-trioxonaphthacene-2-carboxylic acid to produce 5,7,12-trihydroxy-1,2,3,4,6,11-hexahydro-6,11-dioxonaphthacene-2-carboxylic acid;
  m. alkylating 5,7,12-trihydroxy-1,2,3,4,6,11-hexahydro-6,11-naphthacene-2-carboxylic acid to produce 2-methylcarbonyl-5,7,12-trihydroxy-1,2,3,4,6,11-hexahydro-6,11-dioxonaphthacene;
  n. oxidizing 2-methylcarbonyl-5,7,12-trihydroxy-1,2,3,4,6,11-hexahydro-6,11-dioxonaphthacene to produce 5,7,12-trihydroxy-2-acetoxy-1,2,3,4,6,11-hexahydro-6,11-dioxonaphthacene;
  o. hydrolyzing 5,7,12-trihydroxy-2-acetoxy-1,2,3,4,6,11-hexahydro-6,11-dioxonaphthacene to produce 2,5,7,12-tetrahydroxy-1,2,3,4,6,11-hexahydro-6,11-dioxonaphthacene; and
  p. oxidizing 2,5,7,12-tetrahydroxy-1,2,3,4,6,11-hexahydro-6,11-dioxonaphthacene to produce 5,7,12- trihydroxy-1,2,3,4,6,11-hexahydro-2,6,11-trioxonaphthacene.

2. A process for producing 7-methoxy-2,5,12-trihydroxy-1,2,3,4,6,11-hexahydro-6,11-dioxonaphthacene comprising
a. methylating aloe-emodin to produce aloe-emodin 8-methyl ether;
b. halogenating aloe-emodin 8-methyl ether to produce 8-methoxy-1-hydroxy-3-halomethyl-9,10-anthraquinone;
c. reacting 8-methoxy-1-hydroxy-3-halomethyl-9,10-anthraquinone with a dialkyl-2-carbalkoxysuccinate, in which the alkyl and alkoxy groups contain up to about 6 carbon atoms, to produce 8-methoxy-1-hydroxy-3-(2,2,3-trialkoxycarbonylpropyl)-9,10-anthraquinone;
d. saponifying 8-methoxy-1-hydroxy-3-(2,2,3-trialkoxy-carbonylpropyl)-9,10-anthraquinone to produce 8-methoxy-1-hydroxy-3-(2,2,3-tricarboxypropyl)-9,10-anthraquinone;
e. decarboxylating 8-methoxy-1-hydroxy-3-(2,2,3-tricarboxypropyl)-9,10-anthraquinone to produce 8-methoxy-1-hydroxy-3-(2,3-dicarboxypropyl)-9,10-anthraquinone;
f. reducing 8-methoxy-1-hydroxy-3-(2,3-dicarboxypropyl)-9,10-anthraquinone to produce 8-methoxy-1-hydroxy-3-(2,3-dicarboxypropyl)-9,10-(H)-anthr-9-one;
g. cyclizing 8-methoxy-1-hydroxy-3-(2,3-dicarboxypropyl)-9,10-(H)-anthr-9-one to produce 8-methoxy-6-hydroxy-1,2,3,4,7,12-hexahydro-1,7-dioxo-[1,2]-benzanthracene-3-carboxylic acid;
h. oxidizing 8-methoxy-6-hydroxy-1,2,3,4,7,12-hexahydro-1,7-dioxo-[1,2]-benzanthracene-3-carboxylic acid to produce 8-methoxy-6-hydroxy-1,2,3,4,7,12-hexahydro-1,7,12-trioxo-[1,2]-benzanthracene-3-carboxylic acid;
i. oxidizing 8-methoxy-6-hydroxy-1,2,3,4,7,12-hexahydro-1,7,12-trioxo-[1,2]-benzanthracene-3-carboxylic acid to produce 5-methoxy-1,4-dihydroxy-2-(2,3-dicarboxypropyl)-9,10-anthraquinone;
j. reducing 5-methoxy-1,4-dihydroxy-2-(2,3-dicarboxypropyl)-9,10-anthraquinone to produce 8-methoxy-1,4-dihydroxy-3-(2,3-dicarboxypropyl)-9,10-(H)-anthr-9-one;
k. condensing 8-methoxy-1,4-dihydroxy-3-(2,3-dicarboxypropyl)-9,10-(H)-anthr-9-one to produce 7-methoxy-5,12 dihydroxy-1,2,3,4,6,11-hexahydro-4,6-dioxonaphthacene-2-carboxylic acid;
l. oxidizing 7-methoxy-5,12 dihydroxy-1,2,3,4,6,11-hexahydro-4,6-dioxonaphthacene-2-carboxylic acid to produce 7-methoxy-5,12-dihydroxy-1,2,3,4,6,11-hexahydro-4,6,11-trioxonaphthacene-2-carboxylic acid;
m. reducing 7-methoxy-5,12-dihydroxy-1,2,3,4,6,11-hexahydro-4,6,11-trioxonaphthacene-2-carboxylic acid to produce 7-methoxy-5,12-dihydroxy-1,2,3,4,6,11-hexahydro-6,11-dioxonaphthacene-2-carboxylic acid;
n. alkylating 7-methoxy-5,12-dihydroxy-1,2,3,4,6,11-hexahydro-6,11-dioxonaphthacene-2-carboxylic acid to produce 2-methylcarbonyl-7-methoxy-5,12-dihydroxy-1,2,3,4,6,11-hexahydro-6,11-dioxonaphthacene;
o. oxidizing 2-methylcarbonyl-7-methoxy-5,12-dihydroxy-1,2,3,4,6,11-hexahydro-6,11-dioxonaphthacene to produce 7-methoxy-5,12-dihydroxy-2-acetoxy-1,2,3,4,6,11-hexahydro-6,11-dioxonaphthacene; and
p. hydrolyzing 7-methoxy-5,12-dihydroxy-2-acetoxy-1,2,3,4,6,11-hexahydro-6,11-dioxonaphthacene to produce 7-methoxy-2,5,12-trihydroxy-1,2,3,4,6,11-hexahydro-6,11-dioxonaphthacene.

3. A compound having the formula:

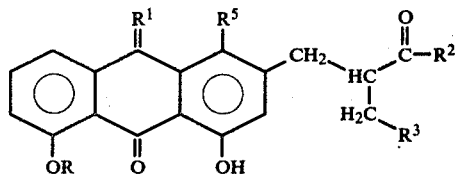

wherein:
R is H or $R^4$;
$R^1$ is O or $H_2$;
$R^2$ is OH or $OR^4$;
$R^3$ is COOH or $COOR^4$;
$R^4$ is a $C_1$ to $C_6$ alkyl group; and
$R^5$ is H or OH.

4. The compound of claim 3 in which R is H, $R^1$ is O, $R^2$ is OH, $R^3$ is COOH, and $R^5$ is OH.

5. The compound of claim 3 in which R is H, $R^1$ is $H_2$, $R^2$ is OH, $R^3$ is COOH, and $R^5$ is H.

6. The compound of claim 3 in which R is H, $R^1$ is O, $R^2$ is OH, $R^3$ is COOH, and $R^5$ is H.

7. The compound of claim 3 in which R is $CH_3$, $R^1$ is O, $R^2$ is OH, $R^3$ is COOH and $R^5$ is OH.

8. The compound of claim 3 in which R is $CH_3$, $R^1$ is $H_2$, $R^2$ is OH, $R^3$ is COOH and $R^5$ is H.

9. The compound of claim 3 in which R is $CH_3$, $R^1$ is O, $R^2$ is OH, $R^3$ is COOH and $R^5$ is H.

10. A compound having the formula:

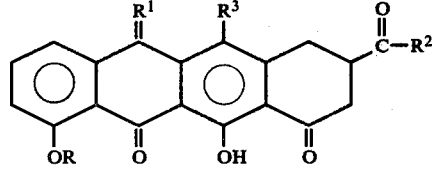

wherein:
R is H or $R^4$;
$R^1$ is O or $H_2$;
$R^2$ is $CH_3$, OH, or $OR^4$;
$R^3$ is H or OH; and
$R^4$ is a $C_1$ to $C_6$ alkyl group.

11. The compound of claim 10 in which R is H, $R^1$ is O, $R^2$ is OH, and $R^3$ is OH.

12. The compound of claim 10 in which R is H, $R^1$ is $H_2$, $R^2$ is OH and $R^3$ is OH.

13. The compound of claim 10 in which R is $CH_3$, $R^1$ is O, $R^2$ is OH, and $R^3$ is OH.

14. The compound of claim 10 in which R is $CH_3$, $R^1$ is $H_2$, $R^2$ is OH and $R^3$ is OH.

15. A compound having the formula:

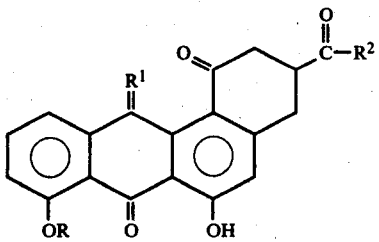

wherein:

R is H or $R^3$;

$R^1$ is O or $H_2$;

$R^2$ is OH or $OR^3$;

$R^3$ is a $C_1$ to $C_6$ alkyl group.

16. The compound of claim 15 in which R is H, $R^1$ is $H_2$, and $R^2$ is OH.

17. The compound of claim 15 in which R is H, $R^1$ is O, and $R^2$ is OH.

18. The compound of claim 15 in which R is $CH_3$, $R^1$ is $H_2$, and $R_2$ is OH.

19. The compound of claim 15 in which R is $CH_3$, $R^1$ is O, and $R^2$ is OH.

20. A compound having the formula:

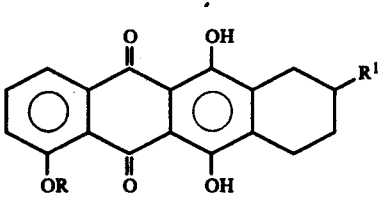

wherein:

R is H or $R^2$;

$R^1$ is COOH, $COOR^2$, or OH; and $R^2$ is a $C_1$ to $C_6$ alkyl group.

21. The compound of claim 20 in which R is H and $R^1$ is COOH.

22. The compound of claim 20 in which R is $CH_3$ and $R^1$ is COOH.

23. A compound having the formula:

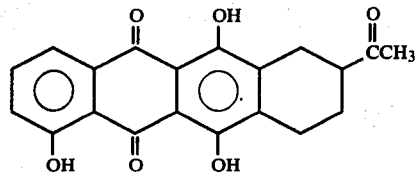

24. The compound of claim 20 in which R is H and $R^1$ is OH.

25. A process for producing 1,8-dihydroxy-3-(2,3-dicarboxypropyl)-9,10-anthraquinone comprising refluxing 1,8-dihydroxy-3-(2,2,3-tricarboxypropyl)-9,10-anthraquinone in an organic solvent in the presence of a strong acid, whereby said 1,8-dihydroxy-3-(2,3-dicarboxypropyl)-9,10-anthraquinone is formed.

26. A process for producing 6,8-dihydroxy-1,2,3,4,7,12-hexahydro-1,7,12-trioxo-[1,2]-benzanthracene-3-carboxylic acid comprising oxidizing, in an aqueous base, 6,8-dihydroxy-1,2,3,4,7,12-hexahydro-1,7 dioxo-[1,2]-benzanthracene-3-carboxylic acid, whereby said 6,8-dihydroxy-1,2,3,4,7,12-hexahydro-1,7,12-trioxo-[1,2]-benzanthracene-3-carboxylic acid is formed.

27. A process for producing 1,4,5-trihydroxy-2-(2,3-dicarboxypropyl)-9,10-anthraquinone comprising subjecting 6,8-dihydroxy-1,2,3,4,7,12-hexahydro-1,7,12-trioxo-[1,2]-benzanthracene-3-carboxylic acid to Baeyer-Villiger oxidization whereby said 1,4,5-trihydroxy-2-(2,3-dicarboxypropyl)-9,10-anthraquinone is formed.

28. A process for producing 8-methoxy-1-hydroxy-3-(2,3-dicarboxypropyl)-9,10-anthraquinone comprising refluxing 8-methoxy-1-hydroxy-3-(2,2,3-tricarboxypropyl)-9,10-anthraquinone in an organic solvent in the presence of a strong acid, whereby said 8-methoxy-1-hydroxy-3-(2,3-dicarboxypropyl)-9,10-anthraquinone is formed.

29. A process for producing 8-methoxy-6-hydroxy-1,2,3,4,7,12-hexahydro-1,7,12-trioxo-[1,2]-benzanthracene-3-carboxylic acid comprising oxidizing, in an aqueous base, 8-methoxy-6-hydroxy-1,2,3,4,7,12-hexahydro-1,7-dioxo-[1,2]-benzanthracene-3-carboxylic acid whereby said 8-methoxy-6-hydroxy-1,2,3,4,7,12-hexahydro-1,7,12-trioxo-[1,2]-benzanthracene-3-carboxylic acid is formed.

30. A process for producing 5-methoxy-1,4-dihydroxy-2-(2,3-dicarboxypropyl)-9,10-anthraquinone comprising subjecting 8-methoxy-6-hydroxy-1,2,3,4,7,12-hexahydro-1,7,12-trioxo-[1,2]-benzanthracene-3-carboxylic acid to Baeyer-Villiger oxidization whereby said 5-methoxy-1,4-dihydroxy-2-(2,3-dicarboxypropyl)-9,10-anthraquinone is formed.

* * * * *